United States Patent
Seely et al.

(10) Patent No.: US 6,982,342 B2
(45) Date of Patent: Jan. 3, 2006

(54) AMMOXIDATION OF CARBOXYLIC ACIDS TO A MIXTURE OF NITRILES

(75) Inventors: Michael J. Seely, Naperville, IL (US); Sanjay P. Godbole, Solon, OH (US); Christos Paparizos, Willowick, OH (US)

(73) Assignee: Standard Oil Company, Warrenville, IL (US)

( * ) Notice: Subject to any disclaimer, the term of this patent is extended or adjusted under 35 U.S.C. 154(b) by 59 days.

(21) Appl. No.: 10/438,586

(22) Filed: May 15, 2003

(65) Prior Publication Data

US 2003/0219372 A1 Nov. 27, 2003

Related U.S. Application Data

(60) Provisional application No. 60/381,066, filed on May 16, 2002.

(51) Int. Cl.
*C07C 253/18* (2006.01)
*C07C 253/24* (2006.01)
(52) U.S. Cl. .................. 558/319; 558/320; 558/323
(58) Field of Classification Search ........... 558/320, 558/323, 319
See application file for complete search history.

(56) References Cited

U.S. PATENT DOCUMENTS

| | | | | |
|---|---|---|---|---|
| 4,316,856 | A | * | 2/1982 | Guttmann et al. ........... 558/322 |
| 5,288,473 | A | | 2/1994 | Shaw et al. ................. 423/237 |
| 5,801,266 | A | | 9/1998 | Ishii ........................... 558/320 |
| 6,013,825 | A | * | 1/2000 | Someya et al. ............. 558/324 |
| 6,204,407 | B1 | * | 3/2001 | Godbole et al. ............ 558/319 |
| 6,413,485 | B2 | | 7/2002 | Seely et al. ................. 423/376 |
| 2001/0006614 | A1 | | 7/2001 | Nero et al. .................. 423/238 |

FOREIGN PATENT DOCUMENTS

| | | |
|---|---|---|
| EP | 0807622 | 11/1997 |
| EP | 0970942 | 1/2000 |
| GB | 1214882 | 12/1970 |
| JP | 2003064042 | 7/2001 |

* cited by examiner

*Primary Examiner*—Johann Richter
*Assistant Examiner*—Ebenezer Sackey
(74) *Attorney, Agent, or Firm*—James R. Henes; David P. Yusko

(57) ABSTRACT

A process for increasing the yield of acetonitrile produced during the manufacture of acrylonitrile comprising introducing a hydrocarbon selected from the group consisting of propylene and propane, a carboxylic acid, ammonia and air into a reaction zone containing an ammoxidation catalyst, reacting the hydrocarbon, carboxylic acid, ammonia and oxygen over said catalyst at an elevated temperature to produce acrylonitrile, hydrogen cyanide and acetonitrile, and recovering the acrylonitrile, hydrogen cyanide and acetonitrile from the reactor.

22 Claims, No Drawings

AMMOXIDATION OF CARBOXYLIC ACIDS TO A MIXTURE OF NITRILES

This application claims the benefit of U.S. Provisional Patent Application Ser. No. 60/381,066 filed on May 16, 2002.

BACKGROUND OF THE INVENTION

Acrylonitrile is an important commodity chemical used mainly as monomer for the manufacture of a wide variety of polymeric materials such as polymers for acrylic fibers used in textiles, and in resins such as ABS and SAN resins. Worldwide, acrylonitrile is produced in amounts exceeding four million metric tons per year. The most commonly used process for manufacturing acrylonitrile is to react a suitable hydrocarbon such as propylene or propane in an ammoxidation reactor in the presence of ammonia using air or other source of molecular oxygen as an oxidant. Such oxidation reactions, also called ammoxidation reactions, typically use a solid-particulate heterogeneous catalyst in a fluidized catalyst bed to catalyze the ammoxidation reaction and provide the desired acrylonitrile in acceptable conversion and yield. In addition to producing acrylonitrile, such ammoxidation reactions also generally produce acetonitrile, hydrogen cyanide (HCN) and other valuable co-products. Acetonitrile is used, for example, as a solvent. Process for the catalytic ammoxidation of a hydrocarbon feed to acrylonitrile are disclosed, for example, in U.S. Pat. Nos. 5,093,299; 4,863,891; 4,767,878; 4,503,001, all of which are incorporated herein by reference.

The processes widely used in commercial practice for recovering the products of such hydrocarbon ammoxidation, such as the ammoxidation of propylene, generally comprise the steps of: a) contacting the effluent from an ammoxidation reactor in a quench tower with an aqueous quench liquid to cool the gaseous effluent; b) contacting the quenched effluent with water in an absorber, forming an aqueous solution comprising the ammoxidation products; c) subjecting the aqueous solution to a water extractive distillation, and d) removing a first overhead vapor stream comprising acrylonitrile and some water from the top of the column, and collecting a liquid waste stream containing water and contaminants from the bottom of the column. Further purification of the acrylonitrile may be accomplished by passing the overhead vapor stream to a second distillation column to remove at least some impurities from the crude acrylonitrile, and further distilling the partially purified acrylonitrile. The effluent from the ammoxidation reactor generally contains a certain amount of ammonia. Therefore, the quench fluid used in the quench tower may also contain a strong mineral acid, such as sulfuric acid, to react with and thereby form the water soluble salt of ammonia, such as ammonium sulfate. The used or spent quench fluid containing the ammonium sulfate and other components is typically treated or disposed of in an environmentally safe manner.

Crude acetonitrile can be obtained as a bottoms stream from a column used to perform the above-mentioned extractive distillation and can then be subjected to further purification procedures such as, for example, the purification procedures disclosed in U.S. Pat. No. 6,204,407.

It would be desirable to be able to adjust the relative amounts of acrylonitrile and acetonitrile produced by the ammoxidation of a hydrocarbon feed material such as propylene or propane because, at times, it is desirable to have additional acetonitrile available to meet changing or increased market demands. Additionally, it would be desirable to produce a spent or used quench liquid that can be recycled within the process for producing acrylonitrile rather than treating for disposal. The present invention provides such processes.

The present invention relates to a process for the ammoxidation of carboxylic acids, especially a mixture of carboxylic acids, to a nitrile or mixture of nitrites. The present invention also relates to increasing the yield and, preferably, the ratio of co-product acetonitrile to acrylonitrile produced during the ammoxidation of a hydrocarbon such as propylene or propane to acrylonitrile.

The present invention also relates to a process which increases the yield of co-product acetonitrile during the manufacture of acrylonitrile by the ammoxidation of a hydrocarbon feed material such as propylene or propane while saving on the raw material costs associated with the increase in co-product yields. The relative amounts of acetonitrile can be controlled by the process of this invention by adjusting the amount of carboxylic acid added to the ammoxidation reaction.

It has been found, unexpectedly, that the use of carboxylic acids, especially crude carboxylic acid mixtures, can attain a desirable increase in the production of acetonitrile during the production of acrylonitrile.

The present invention also relates to a process for recycling spent quench tower quench liquid to the ammoxidation reactor.

SUMMARY OF THE INVENTION

The present invention comprises a process for substantially increasing the yields of acetonitrile produced during the manufacture of acrylonitrile from propylene or propane, or a mixture thereof. Thus, the present invention comprises a process for increasing the yield of co-product acetonitrile produced during the manufacture of acrylonitrile comprising introducing reactants comprising at least one hydrocarbon selected from the group consisting of propylene and propane, a carboxylic acid, ammonia and a molecular oxygen-containing gas into a reaction zone, for example, a fluid bed reactor, containing an ammoxidation catalyst, reacting the hydrocarbon, carboxylic acid, ammonia and oxygen over said catalyst at an elevated temperature to produce acrylonitrile, hydrogen cyanide and acetonitrile, and recovering a product comprising acrylonitrile, hydrogen cyanide and acetonitrile from the reaction zone.

The present invention comprises a process for the conversion of a carboxylic acid, particularly a crude carboxylic acid, and more particularly a mixture of crude carboxylic acids, into a mixture comprising acetonitrile during the manufacture of acrylonitrile without substantially affecting the yield of the acrylonitrile. Thus, the present invention comprises introducing reactants comprising at least one hydrocarbon selected from the group consisting of propylene and propane, at least one carboxylic acid, ammonia and a molecular oxygen-containing gas into a reaction zone, for example, a fluid bed reactor, containing an ammoxidation catalyst, and reacting the hydrocarbon, carboxylic acid, ammonia and molecular oxygen over said catalyst at an elevated temperature to produce acrylonitrile, hydrogen cyanide and acetonitrile.

The present invention comprises introducing at least one of the hydrocarbons selected from the group consisting of propylene and propane, at least one carboxylic acid, ammonia and a molecular oxygen-containing gas into a reaction zone, for example, a fluid bed reactor, to react in the presence of an ammoxidation catalyst, for example, a fluid bed ammoxidation catalyst, to produce a reactor effluent comprising acrylonitrile, hydrogen cyanide and acetonitrile, passing the reactor effluent comprising acrylonitrile, hydrogen cyanide and acetonitrile into a quench column to cool the reactor effluent, and recovering desired product or products comprising at least one of acrylonitrile, acetonitrile and hydrogen cyanide from the reactor effluent.

In one embodiment of the present invention, one or more carboxylic acids can be added to the quench liquid to react with excess ammonia present in the effluent from the ammoxidation reactor. Preferably, at least part of the quench liquid comprising the ammonium salt formed by the reaction of the ammonia with the one or more carboxylic acids is recycled to the ammoxidation reactor or reaction zone.

The products formed by the process of this invention, such as acrylonitrile, acetonitrile and hydrogen cyanide can be recovered and purified by a process known to those of skill in the art such as, for example, the processes disclosed in U.S. Pat. Nos. 4,234,501; 3,885,928; 3,352,764; 3,198,750 and 3,044,966, all of which are incorporated by reference herein.

In the preferred embodiments of the present invention, a crude carboxylic acid is used as the source of carboxylic acid. As used herein, crude carboxylic acid includes a carboxylic acid or mixture thereof that has not been purified to normal, commercially acceptable specifications for pure grade carboxylic acids, and it preferably means a carboxylic acid or mixture thereof produced by one or more processes for the preparation of carboxylic acids but has not been purified to normal commercially acceptable specifications for pure grade carboxylic acids. The crude carboxylic acid or mixture can contain water, other impurities or both. For example, the water content of the crude carboxylic acid can be from about 2, from about 5, or from about 10 weight percent, up to about 98 weight percent. Crude acetic acid is the preferred carboxylic acid used in the embodiments of this invention.

Any ammoxidation catalyst can be used in the embodiments of this invention. Typical ammoxidation catalysts can be generalized by the following two formulae:

$A_aB_bC_cD_dMo_{12}O_x$ where

A=Li, Na, K, Cs, Tl and combinations thereof, preferably Cs and K

B=Ni, Co, Mn, Mg, Ca and combinations thereof, preferably Ni, Co and Mg

C=Fe, Cr, Ce, Cu, V, Sb, W, Sn, Ga, Ge, In, P and combinations thereof, preferably Fe, Cr and Ce D=Bi and/or Te, preferably Bi a=0.1–4.0, preferably 0.1 to 0.5, especially preferred being 0.1 to 0.2 b=0.1–10.0, preferably 5 to 9, especially preferred being 6 to 8, and c,d=0.1–10.0, preferably 0.5 to 4, especially preferred being 0.5 to 3; and $A_aB_bSb_{12}O_x$ where A=Fe, Cr, Ce, V, U, Sn, Ti, Nb and combinations thereof, preferably Fe, V, Sn and Ti B=Mo, W, Co, Cu, Te, Bi, Zn, B, Ni, Ca, Ta and combinations thereof, preferably Mo and Cu a=0.1–16, preferably 2 to 12, especially preferred being 4 to 10 b=0.0–12, preferably 1 to 10, especially preferred being 2 to 6, and the value of x depends on the oxidation state of the elements used.

The suitable ammoxidation catalysts used in this invention can be used either unsupported, or can be supported with silica, alumina, titania, zirconia and the like; however, silica is the preferred support. Examples of catalysts suitable for use in the practice of the present invention are disclosed in U.S. Pat. Nos. 3,642,930; 4,485,079; 3,911,089; 4,873,215; 5,134,105 and 5,093,299, herein incorporated by reference.

DETAILED DESCRIPTION OF THE INVENTION

The present invention is a process for the ammoxidation of a mixture comprising one or more of propylene and propane, ammonia, a source of molecular oxygen and a carboxylic acid. The carboxylic acid is preferably a crude carboxylic acid or mixture of crude carboxylic acids. The present invention is a process for the utilization of carboxylic acids, particularly crude carboxylic acids, as a feed material for the production of a useful nitrile co-product such as acetonitrile produced during the manufacture of acrylonitrile. In addition, a carboxylic acid or mixture thereof containing substantial amounts of a diluent such as water may be utilized in the practice of the present invention, thereby further reducing the cost of the carboxylic acid or carboxylic acid-containing raw materials suitable for the production of co-products.

The present invention is also a process for increasing the yield of acetonitrile during the manufacture of acrylonitrile comprising introducing reactants comprising at least one hydrocarbon selected from the group consisting of propylene and propane, at least one carboxylic acid, ammonia and a molecular oxygen-containing gas such as air, into a reaction zone containing an ammoxidation catalyst, reacting the hydrocarbon, carboxylic acid or acid mixture, ammonia and molecular oxygen over said catalyst at an elevated temperature to produce products comprising acrylonitrile, hydrogen cyanide and acetonitrile, and recovering one or more products comprising one or more of the acrylonitrile, hydrogen cyanide and acetonitrile from the reactor.

Preferred carboxylic acids used in this invention are relatively low carbon number carboxylic acids such as those having 8 or less carbon atoms, preferably 6 or less carbon atoms and most preferably 3 or less carbon atoms. The carboxylic acids can be saturated or unsaturated, branched or linear and can be aromatic or have an aromatic component. The carboxylic acids useful in this invention can be monocarboxylic acids or they can be polycarboxylic acids, that is, have multiple acid groups and thus can be, for example, di-, tri-, tetra-carboxylic acids. Suitable carboxylic acids include, for example, one or more of formic, acetic, propionic, butanoic, oxalic, acrylic, butenoic, maleic, succinic, adipic, benzoic acid, toluic acid and the like. As used herein crude carboxylic acid, such as crude acetic acid, may be a single carboxylic acid that is no more than about 98 weight percent pure, preferably no more than about 95 weight percent pure, more preferably no more than about 90 weight percent pure. Preferably the carboxylic acid used in this invention is acetic acid, more preferably crude acetic acid. Another preferred carboxylic acid used in this invention is a mixture comprising formic, acetic and propionic acid; for example, such a mixture obtained as a side product or waste stream from the manufacture of acetic acid. A crude acid mixture comprising about 5 and up to about 98, or up to about 95 or up to about 90 or 55 weight percent acetic acid, about 0, or about 1, or about 10 up to about 25 weight percent formic acid, and about 0 or about 1 and up to about 20, or up to about 10, or up to about 5 weight percent propionic acid, can be used in the process of this invention.

Such mixtures of crude carboxylic acid can be obtained as a waste or side stream from the manufacture of pure acetic acid.

In the process of this invention some or all of the carboxylic acid can be added as a salt, preferably the salt formed by combining the carboxylic acid with an amine or ammonia. The preferred salt is an ammonium salt. If the carboxylic acid is added where part or all of it is a salt, such as an ammonium salt, the salt is preferably added to the ammoxidation reactor as an aqueous solution. For example, an aqueous solution that is up to about 33 weight percent salt, preferably about 5 to about 33 weight percent ammonium salt. When an aqueous solution is used, the aqueous solution is preferably sprayed into the ammoxidation reaction zone, for example, a fluidized bed of ammoxidation catalyst. A preferred concentration of such ammonium salt is a concentration that is about the same as a recycle stream available from a quench operation used in the process of recovering acrylonitrile from the effluent of an ammoxidation reactor. In such quench operation as described above, the hot gaseous effluent from an ammoxidation reactor is contacted with a quench liquid, preferably an aqueous quench liquid, to cool the ammoxidation reactor effluent. During the quench process, excess ammonia in the ammoxidation reactor effluent can be reacted with a carboxylic acid or mixture of carboxylic acids added to the aqueous quench liquid to form a carboxylic acid-ammonia salt, that is, an ammonium salt. Used or spent quench liquid obtained from such quench operation comprising such ammonium salt of a carboxylic acid or mixture thereof, is a preferred source of carboxylic acid of this invention for adding to the ammoxidation reactor in accordance with this invention. The carboxylic acid or acids added to the quench liquid to react with and remove excess ammonia can be one or more of the carboxylic acids or mixture thereof described hereinabove. Thus, in an embodiment of this invention, a carboxylic acid or mixture thereof, preferably one or more of the carboxylic acids described hereinabove, is added to the quench liquid, preferably an aqueous quench liquid, used to quench the effluent from an ammoxidation reactor for the manufacture of acrylonitrile. After being used to quench the ammoxidation reactor effluent and to react with the ammonia present in the ammoxidation reactor effluent, the liquid comprising the ammonium salt of the carboxylic acid or mixture thereof is at least in part recycled to the ammoxidation reactor. The amount of carboxylic acid-ammonium salt in such recycled quench liquid can be about 5 up to about 33, more preferably up to about 15 weight percent ammonium salt of a carboxylic acid. The preferred carboxylic acid added to the quench liquid is acetic acid, preferably crude acetic acid. Another preferred carboxylic acid is the mixture, as described hereinabove, comprising formic, acetic and propionic acid. Preferred are such mixtures where the amount of propionic acid is low, for example, no more than 5 weight percent, more preferably no more than 1 weight percent of the mixture. The quench, liquid, preferably the aqueous quench liquid, is preferably added to the ammoxidation reactor by spraying the quench liquid into the reactor, preferably into the fluidized bed of a fluidized bed reactor.

The amount of carboxylic acid or mixture thereof added to the reaction zone in the process of this invention, added in the form of a carboxylic acid or as a salt, such as the ammonium salt, can be up to about 50 percent, or up to about 25 or 40 percent, for example between about 1 and about 15 percent, of the ammonia feed rate to the reaction zone on a mole basis.

In the preferred embodiment of the present invention, the ammoxidation reactor conditions can be adjusted to obtain the increased yield in acetonitrile obtained by utilizing the carboxylic acid or mixture thereof. In the practice of the present invention, the ammoxidation reaction conditions are preferably within the following parameters: the feed rate of carboxylic acid or mixture thereof, added in the form of a carboxylic acid or as a salt, such as the ammonium salt, can be up to about 50 percent, or up to about 25 or 40 percent, for example between about 1 and about 15 percent, of the ammonia feed rate on a mole basis, the temperature of the ammoxidation reaction can be between about 420° to about 460° C., preferably about 430° to about 440° C., the pressure is suitably maintained at between about 1 to about 2 atmospheres, preferably about 1 to about 1.2 or about 1.1 atmospheres.

In the preferred embodiments of the present invention, the process is performed in a fluid bed reactor using a particulate ammoxidation catalyst.

EXAMPLES

The following examples are set forth below for illustrative purposes and are not considered as limiting to the practice of the present invention.

Ammoxidation reactions of propylene using air and ammonia were conducted with and without the addition of a carboxylic acid. The catalyst utilized in all of the examples was a promoted $BiFeMoO_x$ known for its suitability in the ammoxidation of propylene to acrylonitrile. Crude acetic acid in the amount of 2.5, 5 and 10% of the ammonia feed on a molar basis was added to an ammoxidation reactor along with propylene and air to give the results set forth below in Table I. The crude acetic acid mixture was brought to pH 5 by the addition of ammonium hydroxide solution and the resulting acid diluted to 67% water before being fed to the reactor. In each of the following examples, the reactor temperature was 440° C., the pressure was 10.0 psig and the molar feed ratio of propylene/ammonia/air/acid was 1/1.17/10.0/X (X=0.029, 0.059, 0.12). The wwh was 0.08 (grams of hydrocarbon/grams of catalyst, hour).

TABLE I

| Example No. | Acetic Acid as Mole % of Ammonia Feed | % Acrylonitrile Yield | % Acetonitrile Yield | % HCN Yield |
| --- | --- | --- | --- | --- |
| 1(comp.) | 0 | 79.6 | 1.5 | 6.1 |
| 2 | 2.5 | 80.1 | 2.2 | 5.9 |
| 3 | 5 | 78.7 | 2.8 | 5.8 |
| 4 | 10 | 77.3 | 3.9 | 6.0 |

The data in Table 1 demonstrate that the addition of acetic acid to the ammoxidation reaction results in an increase in the yield of acetonitrile produced.

In general, all carboxylic acids can be ammoxidized to a mixture of nitrites. In particular, acetic acid and preferably crude acetic acid can be ammoxidized to acetonitrile. Preferred acids include $C_1$ to $C_4$ carboxylic acids.

This invention is also a process comprising introducing reactants comprising at least one carboxylic acid, ammonia and a molecular oxygen-containing gas into a reaction zone, for example a fluid bed reactor, containing an ammoxidation catalyst, such as one of the catalysts described herein, and reacting, using temperatures and pressures such as those described herein, the reactants comprising the carboxylic acid, ammonia and molecular oxygen over said catalyst at an elevated temperature to produce a product comprising a nitrile, preferably where the carboxylic acid comprises acetic acid, more preferably where the carboxylic acid comprises crude acetic acid, and when the carboxylic acid comprises acetic acid or crude acetic acid the nitrile preferably comprises acetonitrile.

Only certain embodiments and examples of the invention have been set forth and alternative embodiments and various modifications will be apparent from the above description to those of skill in the art. These and other alternatives are considered equivalents and within the spirit and scope of the invention.

U.S. Provisional Patent Application Ser. No. 60/381,066 filed on May 16, 2002, is incorporated hereby by reference in its entirety.

That which is claimed is:

1. A process comprising introducing reactants comprising at least one hydrocarbon selected from the group consisting of propylene and propane, at least one carboxylic acid, ammonia and a molecular oxygen-containing gas into a reaction zone containing an ammoxidation catalyst, and reacting the reactants comprising the hydrocarbon, carboxylic acid, ammonia and molecular oxygen over said catalyst at an elevated temperature to produce a product comprising acrylonitrile, hydrogen cyanide and acetonitrile.

2. The process of claim 1 wherein the carboxylic acid comprises a crude carboxylic acid.

3. The process of claim 1 wherein the carboxylic acid comprises a mixture of carboxylic acids.

4. The process of claim 1 wherein the carboxylic acid is at least partially in the form of an ammonium salt.

5. The process of claim 1 wherein the carboxylic acid is at least partially in the form of a salt of an amine.

6. The process of claim 4 wherein the ammonium salt comprises an aqueous solution.

7. The process of claim 1 wherein the carboxylic acid comprises acetic acid.

8. The process of claim 1 wherein the carboxylic acid comprises crude acetic acid.

9. The process of claim 1 wherein the carboxylic acid comprises a mixture of formic, acetic and propionic acids.

10. The process of claim 6 wherein the carboxylic acid comprises crude acetic acid.

11. A process comprising introducing reactants comprising ammonia, a molecular oxygen-containing gas, and at least one hydrocarbon selected from the group consisting of propylene and propane into a reaction zone containing an ammoxidation catalyst, reacting the reactants comprising the hydrocarbon, ammonia and molecular oxygen over the catalyst at an elevated temperature to produce a reaction zone effluent comprising acrylonitrile, hydrogen cyanide and acetonitrile, contacting the reaction zone effluent with a quench liquid comprising water and a carboxylic acid, and adding at least a portion of the quench liquid to the reaction zone after the quench liquid is contacted with the reaction zone effluent.

12. The process of claim 11 wherein the carboxylic acid comprises a crude carboxylic acid.

13. The process of claim 11 wherein the carboxylic acid comprises a mixture of carboxylic acids.

14. The process of claim 11 wherein the carboxylic acid comprises a mixture of formic, acetic and propionic acids.

15. The process of claim 11 wherein the quench liquid added to the reaction zone comprises the ammonium salt of the carboxylic acid.

16. A process for increasing the yield of co-product acetonitrile produced during the manufacture of acrylonitrile comprising introducing reactants comprising at least one hydrocarbon selected from the group consisting of propylene and propane, a carboxylic acid, ammonia and a molecular oxygen-containing gas into a reaction zone containing an ammoxidation catalyst, reacting the reactants comprising the hydrocarbon, carboxylic acid, ammonia and oxygen over said catalyst at an elevated temperature to produce a product comprising acrylonitrile, hydrogen cyanide and acetonitrile.

17. The process of claim 1 wherein the carboxylic acid comprises acetic acid.

18. The process of claim 16 wherein the carboxylic acid comprises crude acetic acid.

19. The process of claim 16 wherein the carboxylic acid comprises a mixture of formic, acetic and propionic acid.

20. The process of claim 16 wherein the carboxylic acid is at least partially in the form of an ammonium salt.

21. The process of claim 11 wherein the carboxylic acid comprises acetic acid.

22. The process of claim 11 wherein the carboxylic acid comprises crude acetic acid.

* * * * *